United States Patent [19]

David

[11] Patent Number: 4,977,522

[45] Date of Patent: Dec. 11, 1990

[54] APPARATUS FOR DETERMINING THE FORMULATION OF PAINT FOR USE IN BODYWORK REPAIR

[76] Inventor: Michel David, 20, Avenue d'Ivry, 75013 Paris, France

[21] Appl. No.: 277,246

[22] Filed: Nov. 29, 1988

[30] Foreign Application Priority Data

Nov. 30, 1987 [FR] France .................................. 87 16601

[51] Int. Cl.$^5$ .......................... G01J 3/50; G01N 21/25
[52] U.S. Cl. ..................................... 364/526; 356/408
[58] Field of Search ................. 364/526, 200 MS File, 364/400 MS File; 356/402, 403, 405–408, 411, 421, 425

[56] References Cited

U.S. PATENT DOCUMENTS

| | | | |
|---|---|---|---|
| 3,026,039 | 3/1962 | Zeyen ................................... | 364/526 |
| 3,601,589 | 9/1969 | McCarty ............................. | 364/526 |
| 3,910,701 | 10/1975 | Henderson et al. .................. | 356/39 |
| 4,439,038 | 3/1984 | Mactaggart ........................ | 364/526 |
| 4,583,858 | 4/1986 | Lebling et al. ..................... | 356/402 |
| 4,653,014 | 3/1987 | Mikami et al. ..................... | 364/526 |
| 4,660,159 | 4/1987 | Ott ....................................... | 364/526 |
| 4,813,000 | 3/1989 | Wyman et al. ..................... | 364/526 |

FOREIGN PATENT DOCUMENTS

| | | |
|---|---|---|
| 0079517 | 5/1983 | European Pat. Off. . |
| 2313528 | 4/1981 | Fed. Rep. of Germany . |
| 8417621 | 1/1986 | Fed. Rep. of Germany . |
| 486692 | 2/1970 | Switzerland . |
| 1229307 | 4/1971 | United Kingdom . |

Primary Examiner—Dale M. Shaw
Assistant Examiner—John A. Merecki
Attorney, Agent, or Firm—Ostrolenk, Faber, Gerb & Soffen

[57] ABSTRACT

An apparatus including a measuring head, equipped with light sources for lighting one part of a bodywork of which the color is to be reproduced with a receiver for picking up the light reflected in each of a plurality of preset wavelength in order to produce a signal representing the reflectance of the surface in each wavelength. The apparatus also includes a device for calculating, for each wavelength, the reflectance for any combination of basic shades or bases from among a predetermined set off bases, and apparatus for continuously comparing the measured reflectance with the calculated reflectance in order to find a suitable paint formulation. A starting formulation given by the particular combination of bases corresponding to the color reference of the bodywork to be repaired may be modified, until the difference between the calculated reflectance values and measured reflectance values reaches a minimum or becomes smaller than a preset threshold.

5 Claims, 2 Drawing Sheets

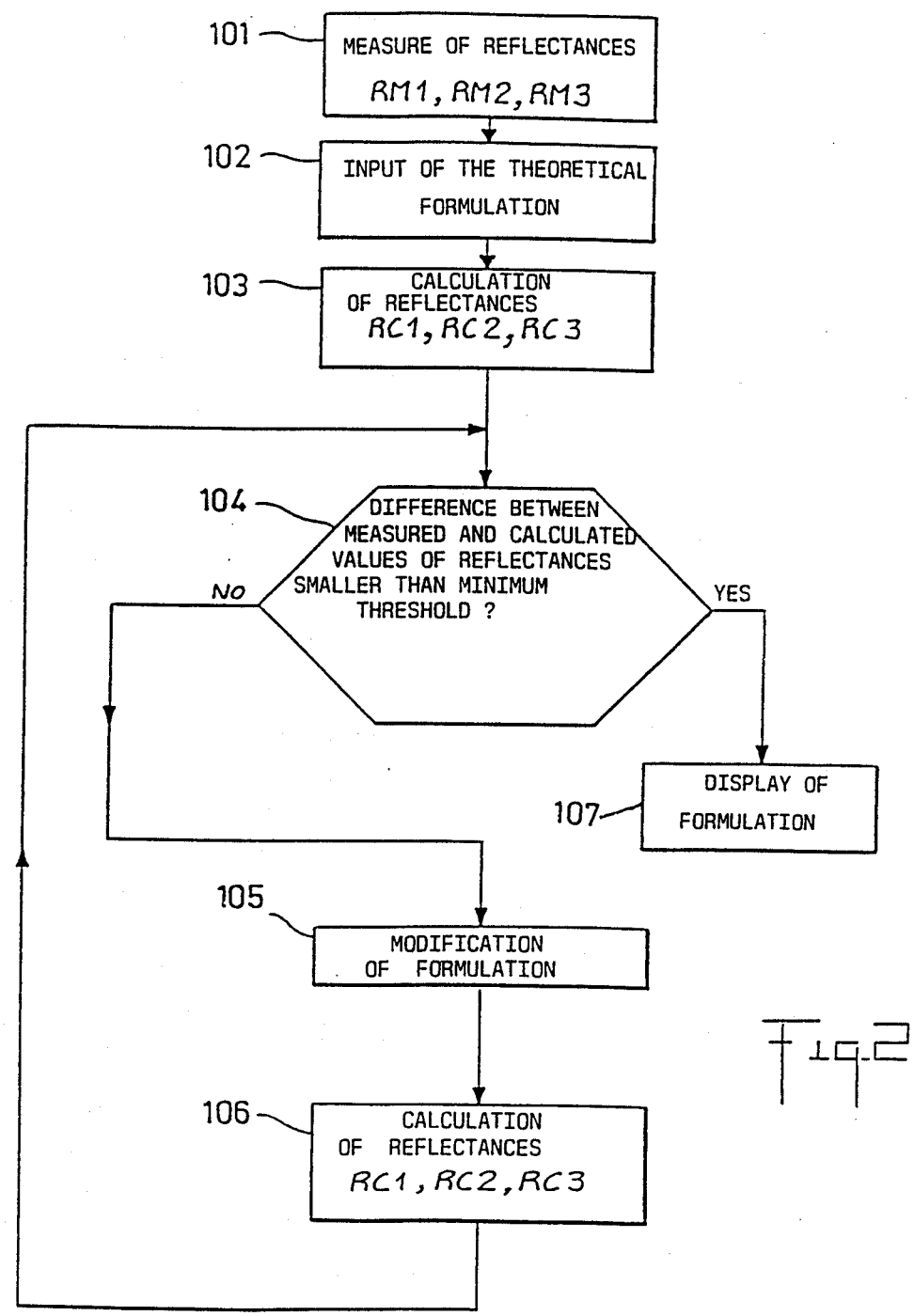

APPARATUS FOR DETERMINING THE FORMULATION OF PAINT FOR USE IN BODYWORK REPAIR

BACKGROUND OF THE INVENTION

The present invention relates to an apparatus for determining a formulation for bodywork paints, in particular for the bodywork of motor vehicles, in order to determine automatically the formulation to use when bodywork repairs involve paint works.

In certain types of motor vehicles, the different bodywork colors are referenced and to each reference corresponds a formula given by the paint manufacturer. Nonetheless, whenever paint works are required after repairs to the bodywork, it is nearly always necessary to modify the formula so that the part of the bodywork which is re-painted does not differ from the rest of the bodywork. One reason is that the color of the bodywork has altered with time. Another reason is that shade differences are unavoidable between paints that are obtained by the same formula but with basic products of different production. In practice, the modification of the formula is done on a trial-and-error basis with tests made on sheet metal plates, sometimes without a completely satisfactory result being obtained.

Certainly, there are photospectrometers which automatically give good formulation for reproducing a color from a set of basic shades or bases, but this equipment is expensive. Moreover, it is not well suited for the application considered herein, especially when the color to be reproduced can only be analyzed by introducing into the apparatus a plate of the same color.

SUMMARY OF THE INVENTION

It is therefore, the object of the present invention to provide an apparatus for determining automatically the adequate paint formulation for bodywork repairs, without having to make repeated trials, which apparatus is of a much lower cost than the existing spectrometers, and which is particularly easy to use in a bodywork repair shop.

According to the invention, such an apparatus comprises:

storing means for storing into a memory information relative to a set of basic shades or bases, and which permits the calculation of the reluctance therefrom, for each of a predetermined number of wavelengths of the visible spectrum, of formulation obtained by combining one or more of said bases, means for recording particular formulations corresponding to bodywork color references and combining one or more of said bases, calculation means for calculating, for each one of the predetermined wavelengths, the reflectance obtained with any combination of the bases, a measuring device comprising a measuring head designed to be applied on one part of the bodywork of which the color is to be reproduced, means for lighting the surface of said bodywork part with lights having said predetermined wavelengths, and at least one receiver for picking up the light reflected by said surface in each predetermined wavelength, for producing a signal representing the reflectance of the surface in each predetermined wavelength, and means for comparing the data representing the measured reflectances with the data representing the calculated reflectances for to identifying the suitable formulation, by successive modifications, starting from a first formulation given by the particular combination of bases corresponding to the color reference of the bodywork to be repaired, until the difference between the calculated reflectance values and the measured reflectance values reaches a minimum or becomes smaller than a given threshold.

A characteristic feature of the invention lies in the fact that the particular combinations of bases corresponding to bodywork color references are recorded, whereby the process o determining the adequate formulation to be used in repairing a bodywork can be carried out starting from a particular combination which comprises a limited number of bases and is substantially near the combination to be determined. The process is considerably simplified compared with systems where the determination of an adequate formulation should he made among the set of all possible bases.

BRIEF DESCRIPTION OF THE DRAWINGS

The invention will be more readily understood on reading the following description with reference to the accompanying drawings, in which:

FIG. 2 illustrates the successive steps in the process for automatic determination of a paint formula.

DETAILED DESCRIPTION OF THE PREFERRED EMBODIMENT

Figure 1:
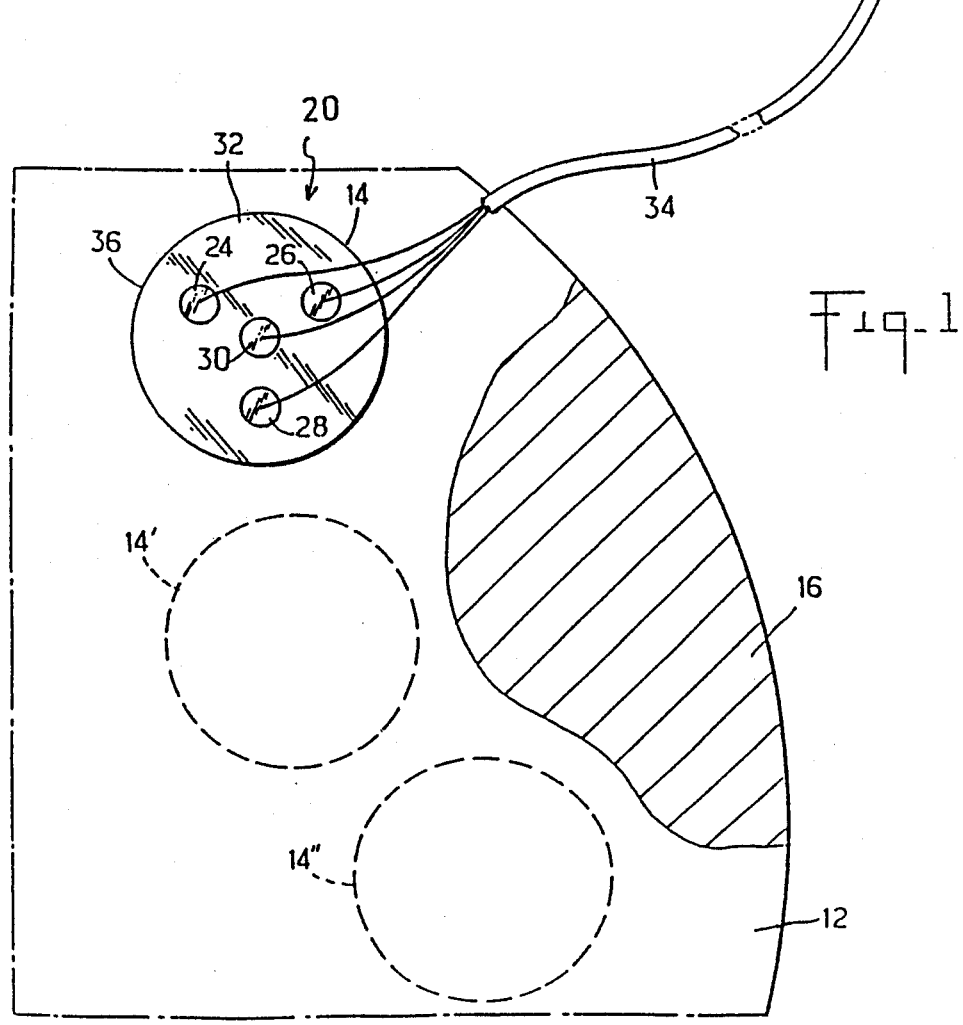
FIG. 1 is a very diagrammatical view of one embodiment of an apparatus according to the invention.

The apparatus 10 illustrated in FIG. 1 is designed for determining the adequate formulation of a paint to be used when repairing a part of a bodywork 12, in this case the bodywork of a motor vehicle.

The apparatus 10 is essentially composed of a reflectance measuring device 20, of a microprocessor device 40 and of peripherals such as a cathode ray tube or video terminal 52, a keyboard 54 and a printer 56.

The reflectance measuring device 20 comprises a plurality of light sources 24, 26, 28 emitting in the visible spectrum and a receiver 30. Said light sources 24, 28, 28 and receiver 30 are mounted on a semi-spherical measuring head 32, as shown in plan view in FIG. 1. Receiver 30 is fixed to the top of head 32 whereas sources 24, 28, 28 are fixed in places angularly distributed at regular intervals around the axis of the head 32 and at the same distance from the top of said head. Sources 24, 26, 28 are, for example, xenon lamps. Three interference filters, not shown in the figures, centered for example on wavelengths 500 nm, 580 nm and 660 nm are interposed between sources 24, 26, 28 and receiver 30, a filter being associated to each source, so as to be able to effect reflectance measurements for three different wavelengths of the visible spectrum. Receiver 30 comprises for example a photodetector which delivers a signal representing the quantity of light received in each wavelength.

Sources 21, 28, 28 are sequentially controlled by signals received from the microprocessor device 40 and the signals issued from receiver 30 are transmitted to said device in order to be converted to digital data representing the quantity of light received.

Advantageously the measuring head is connected to the microprocessor device by a flexible connection 34, this enabling the measuring head to be brought in contact with any target part of the bodywork, regardless of the orientation. The semi-spherical head 32 is applied against the bodywork surface by its circular edge 36, the light beams produced by sources 24, 28, 28 being sent in the direction of the inner side toward the center of the circular opening defined by edge 36.

The measuring device 20 is used for measuring the reflectance of the bodywork surface in one painted zone thereof in order to determine the paint formulation which will be suitable for re-painting another part of said bodywork. Moreover, the reflectance is measured preferably on a painted zone 14, close to the part to be re-painted 16. Preferably, reflectance measurements are taken in several zones 14, 14', 14'' situated around said part 16, and the mean value of the reflectance values measured for the different wavelengths is recorded.

The microprocessor device 40 comprises, in a manner which is known per se, a central microprocessing unit 42, permanent data and programs read-only memories 44 data R/W memories 46, and inputs/outputs circuits 48, these various elements communicating together via bus 50. The communication between device 40 and an operator is achieved via the screen of video terminal 52 associated to keyboard 54. The information, namely the determined paint formulations, are edited by way of a printer 56.

In the data ROM memories are stored data relative to a set of basic shades, or bases, which will help calculating the reflectance for paint formulations combining a certain number of said bases.

Said data consist for example in the values K and S for each wavelength used in the measurements and for each base, K and S being respectively the coefficient of absorption and the coefficient of diffusion. Indeed, the fact of knowing the values K and S for each base, enables the calculation of the reflectance of a painted surface with any combination of said bases, by using Duncan's formula giving the resulting K/S ratio:

$$\left(\frac{K}{S}\right)_\lambda = \frac{\sum_{i=1}^{n} C_i K_i(\lambda)}{\sum_{i=1}^{n} C_i S_i(\lambda)}$$

$\lambda$ being the wavelength considered, n the number of bases, $C_i$ the concentration of the ith base in the formulation, $K_i(\lambda)$ the value of K for the ith base at the wavelength $\lambda$ and $S_i(\lambda)$ the value of S for the ith base at the wavelength. The reflectance R is given by:

$$R = 1 + \frac{K}{S} - \sqrt{\left(\frac{K}{S}\right)^2 + 2\left(\frac{K}{S}\right)}.$$

The method for determining the adequate paint formulation consists, by starting with the formulation corresponding to the bodywork color reference, in modifying that initial formulation until calculated reflectance values are obtained which are substantially identical to the measured reflectance values.

Different successive steps of this method are illustrated in FIG. 2.

A first step (phase 101) consists in measuring the reflectance of the bodywork in a painted zone thereof for every wavelength. This is achieved by successively activating the three sources 24, 26, 28, thus giving three values of measured reflectance RM1, RM2, RM3. As already indicated, several measurements can be taken in different zones situated around the bodywork part to be re-painted, the reflectance value recorded for each wavelength being the mean value among the values obtained in the different zones for said wavelength.

A second step (phase 102) consists in recording the theoretical formulation, i.e. the particular combination of bases corresponding to the color reference of the bodywork of which one part is to be re-painted. This theoretical formulation is supplied by a paint manufacturer, in this case the one who supplies the bases used for each bodywork color reference of all vehicles found on the market. The theoretical formulation consisting in the identification of the different bases included and their relative proportions may be recorded through the keyboard 54 by the person using the apparatus. As a variant, the theoretical formulations for a set of bodywork color references may be stored in permanent portable electronic (PROM) or magnetic (diskettes) storage means, which means enable said references to be loaded directly into the apparatus. In this latter case, the formulations may be updated by periodical supply by the paint manufacturer of new storage means.

A third step (phase 103) consists in calculating the reflectance values RC1, RC2, RC3 (or reading them if they are available with the recorded formulation) for the different wavelengths considered, for the theoretical formulation corresponding to the color reference of the bodywork of which one part is to be re-painted.

Then measured values RM1, RM2, RM3 and calculated values RC1, RC2, RC3 are compared.

If necessary, depending on the result of the comparison (test 104), the formulation is modified either by changing the relative proportions of the bases in the theoretical formulation, or by adding a new base and/or removing one base from the theoretical formulation. The modification of the paint formula (phase 105) may be carried out by hand. In view of the differences recorded between measured values and calculated values of reflectance for the different wavelengths, the operator introduces via the keyboard the modifications that he considers appropriate for the paint formulation.

The reflectance values for the modified paint formula, are calculated for the different wavelengths (phase 106) and substituted to the previous values RC1, RC2, RC3 in order to return to the step of comparison with measured values RM1, RM2, RM3.

Several successive modifications of the paint formula may thus be made until the comparison between calculated values and measured values (test 104) indicates that the difference between said values for each wavelength is below a preset minimum threshold.

The paint formula which has thus been determined can then be displayed on the screen of terminal 52 (phase 107) and/or edited by printer 56.

The foregoing describes a manual method for modifying the paint formula when the differences between the measured values and the calculated values of reflectance exceed the preset minimum thresholds.

Another possibility is to use an automatic modification method by simulating routine. This simulating routine consists in varying by increments, within a preset limit, the concentrations of the bases making up the theoretical formulation, and then in finding out what formulation gives the minimum differences between measured values and calculated values of reflectance for the three wavelengths.

If the minimum differences, determined as indicated above, are found to be greater than a preset threshold, this may be indicated to the user in order to enable him to seek a better formulation by adding and/or taking out one or more bases to or from the theoretical formulation.

Moreover, although the described method uses reflectance measurements and calculations for three wavelengths of the visible spectrum, it is also possible to apply said method with measurements and calculations for only two different wavelengths, or, on the contrary, for more than three different wavelengths.

The advantages of the apparatus as described hereinabove reside in its relatively low production cost, in its readyness of use, and in its adaptability to industrial use.

The recording of theoretical formulations corresponding to different bodywork color references and the use of such theoretical formulations as initial data for the process of determining adequate formulations bring significant advantages. The number of bases in a theoretical formulation corresponding to a color reference is usually limited, for example not larger than 8, and the adequate formulation is generally not very different from the theoretical one. The process of determining the adequate formulation is therefore relatively easy and fast. It would be quite different if the adequate formulation were to be determined among the complete set of all possible bases (their number may be of two dozens or more), without any particular initial combination serving as a starting point for the process.

I claim:

1. An apparatus for determining a color formulation of a paint to be used for color matching in the field of bodywork repair, where a bodywork under repair has paint whose original color formulation is specified in terms of at least one base color paint, and said paint color formulation to be used for color matching is liable to be different from said original paint color formulation due to color drift, said apparatus comprising:

first memory means for storing reflectance data relating to each of a plurality of base color paints;
second memory means for storing at least one of said original paint color formulations;
calculation means cooperating with said first and second memory means for determining a calculated reflectance value, for at least one predetermined wavelength, of a paint formulation composed of at least one of said base color paints;
measuring means comprising a measuring head designed to be applied on one part of said bodywork of which the color is to be reproduced, means for lighting a surface of said bodywork part with lights having said at least one predetermined wavelength, and at least one receiver for picking up the light reflected by said surface in each predetermined wavelength, said receiver producing data representing the reflectance value of the surface in each of said predetermined wavelengths;
comparison means for comparing a measured reflectance value with a calculated reference value, and producing comparison data indicative of a difference between said values;
approximation means cooperating with said calculation means and said comparison means, comprising:
means for formulating at least one calculated paint color; and
means for successively supplying calculated reflectance values to said comparison means, starting with an original calculated reflectance value corresponding to the original paint color formulation of said bodywork under repair, followed by at least one successive calculated reflectance value, the first of which corresponds to a respective first calculated paint color, whereby said respective first calculated paint color, and each successive calculated paint color thereafter, is formulated in response to said comparison data so that the calculated reflectance thereof, for at least one predetermined wavelength, is closer to said measured reflectance value, for a corresponding wavelength, than the previously calculated reflectance value supplied to said comparison means, whereby a final first paint color formulation is derived approximating said paint color formulation to be used.

2. Apparatus as claimed in claim 1, wherein the measuring means comprises a plurality of light sources mounted with the receiver on the measuring head 3. Apparatus as claimed in claim 1, wherein the second memory means for storing at least one of said original paint color formulations comprises portable storing means.

4. Apparatus as claimed in claim 1, wherein the measuring means comprises a plurality of light sources associated with respective filters.

5. Apparatus as claimed in claim 1, wherein three of said predetermined wavelengths are used to determine said paint color formulation.

* * * * *